United States Patent
Gettig

[19]

[11] Patent Number: 5,860,961
[45] Date of Patent: Jan. 19, 1999

[54] HYPODERMIC INJECTOR SYSTEM AND METHOD FOR MAINTAINING THE STERILITY THEREOF PRIOR TO USE

[75] Inventor: William A. Gettig, Millheim, Pa.

[73] Assignee: Gettig Technologies, Incorporated, Spring Mills, Pa.

[21] Appl. No.: 816,392

[22] Filed: Mar. 13, 1997

Related U.S. Application Data

[62] Division of Ser. No. 661,260, Jun. 10, 1996, Pat. No. 5,718,690.

[51] Int. Cl.⁶ .................................................. A61M 5/00
[52] U.S. Cl. ........................... 604/199; 604/218; 604/232
[58] Field of Search .................................. 604/199, 218, 604/110, 232, 221, 900; 128/763–765

[56] References Cited

U.S. PATENT DOCUMENTS

| | | | |
|---|---|---|---|
| 144,661 | 11/1873 | Cutter . | |
| 405,100 | 6/1889 | Kloppe . | |
| 1,217,630 | 2/1917 | Powers . | |
| 1,687,324 | 10/1928 | Cook . | |
| 1,747,243 | 2/1930 | Hoskins . | |
| 2,270,536 | 6/1981 | Lemelson | 128/218 |
| 2,431,406 | 11/1947 | Lasersohn | 128/218 |
| 2,538,390 | 1/1951 | Smith | 128/215 |
| 2,616,420 | 11/1952 | Hart | 128/218 |
| 2,661,740 | 12/1953 | Hickey | 128/218 |
| 2,693,803 | 11/1954 | Ogle | 128/218 |
| 2,728,341 | 12/1955 | Roehr | 128/218 |
| 2,826,195 | 3/1958 | Ashkenaz | 128/218 |
| 2,855,927 | 10/1958 | Henderson | 128/218 |
| 2,880,723 | 4/1959 | Adams | 128/215 |
| 3,375,825 | 4/1968 | Keller | 128/221 |
| 3,500,828 | 3/1970 | Podhora | 128/214.4 |
| 3,534,734 | 10/1970 | Budreck | 128/218 |
| 3,783,997 | 1/1974 | Brown | 206/43 |
| 3,916,893 | 11/1975 | De Felice | 128/218 R |
| 4,186,750 | 2/1980 | Patel | 128/748 |
| 4,207,870 | 6/1980 | Eldridge | 128/766 |
| 4,317,445 | 3/1982 | Robinson | 128/214.4 |
| 4,326,541 | 4/1982 | Eckels | 128/766 |
| 4,340,068 | 7/1982 | Kaufman | 128/766 |
| 4,610,671 | 9/1986 | Luther | 604/168 |
| 4,692,156 | 9/1987 | Haller | 604/195 |
| 4,808,169 | 2/1989 | Haber et al. | 604/195 |
| 4,834,717 | 5/1989 | Haber et al. | 604/193 |
| 4,874,373 | 10/1989 | Luther et al. | 604/164 |
| 4,894,052 | 1/1990 | Crawford | 604/63 |
| 4,919,652 | 4/1990 | Alter et al. | 604/110 |
| 4,950,253 | 8/1990 | Jacobs | 604/218 |
| 5,064,419 | 11/1991 | Garde | 604/195 |
| 5,098,395 | 3/1992 | Fields | 604/168 |
| 5,120,319 | 6/1992 | Van Heugten et al. | 604/168 |
| 5,151,088 | 9/1992 | Allison et al. | 604/192 |
| 5,205,824 | 4/1993 | Mazur | 604/110 |
| 5,242,414 | 9/1993 | Fischell et al. | 604/168 |
| 5,242,419 | 9/1993 | Kiner et al. | 604/195 |
| 5,250,035 | 10/1993 | Smith et al. | 604/164 |
| 5,256,154 | 10/1993 | Liebert et al. | 604/199 |
| 5,267,971 | 12/1993 | Brimhall | 604/177 |
| 5,295,969 | 3/1994 | Fischell et al. | 604/168 |
| 5,306,258 | 4/1994 | de la Fuente | 604/110 X |
| 5,312,376 | 5/1994 | Van Heugten | 604/272 |
| 5,370,621 | 12/1994 | Godat et al. | 604/199 |
| 5,380,295 | 1/1995 | Vacca | 604/199 X |
| 5,496,281 | 3/1996 | Krebs | 604/168 |
| 5,520,193 | 5/1996 | Suzuki et al. | 128/764 |

FOREIGN PATENT DOCUMENTS

| | | |
|---|---|---|
| 879398 | 1/1980 | Belgium . |
| 0079498 | 5/1983 | European Pat. Off. . |
| 196481 | 6/1938 | Switzerland . |
| 1002348 | 9/1965 | United Kingdom . |
| 1910695 | 10/1969 | United Kingdom . |
| 8902760 | 4/1989 | WIPO . |

*Primary Examiner*—John D. Yasko
*Attorney, Agent, or Firm*—Kirkpatrick & Lockhart LLP

[57] ABSTRACT

A syringe for use in connection with a pre-filled medicament cartridge that is sealed on one end by a pierceable seal and on the other end by a plunger supported therein. The syringe includes a plunger rod for axially advancing the plunger within the cartridge to discharge the medicament therefrom. The plunger rod is also attachable to the syringe body prior to use. A sheath is provided to cover the portion of the double ended cannula that protrudes from the syringe body. The sterile syringe body/plunger rod and sheath assembly serve to maintain the sterility of the cannula prior to use.

9 Claims, 15 Drawing Sheets

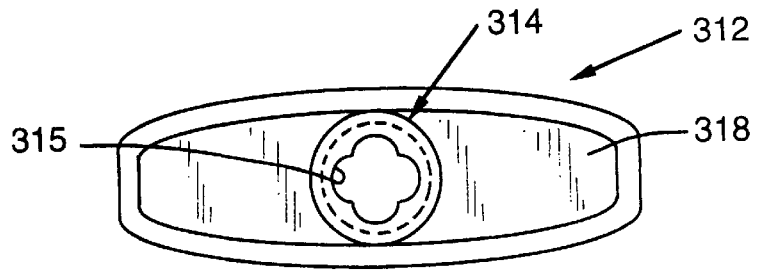
FIG. 15
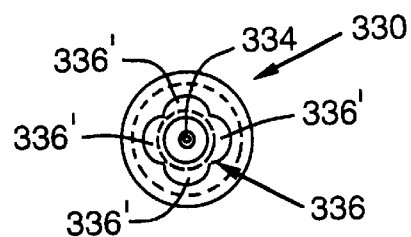
FIG. 16
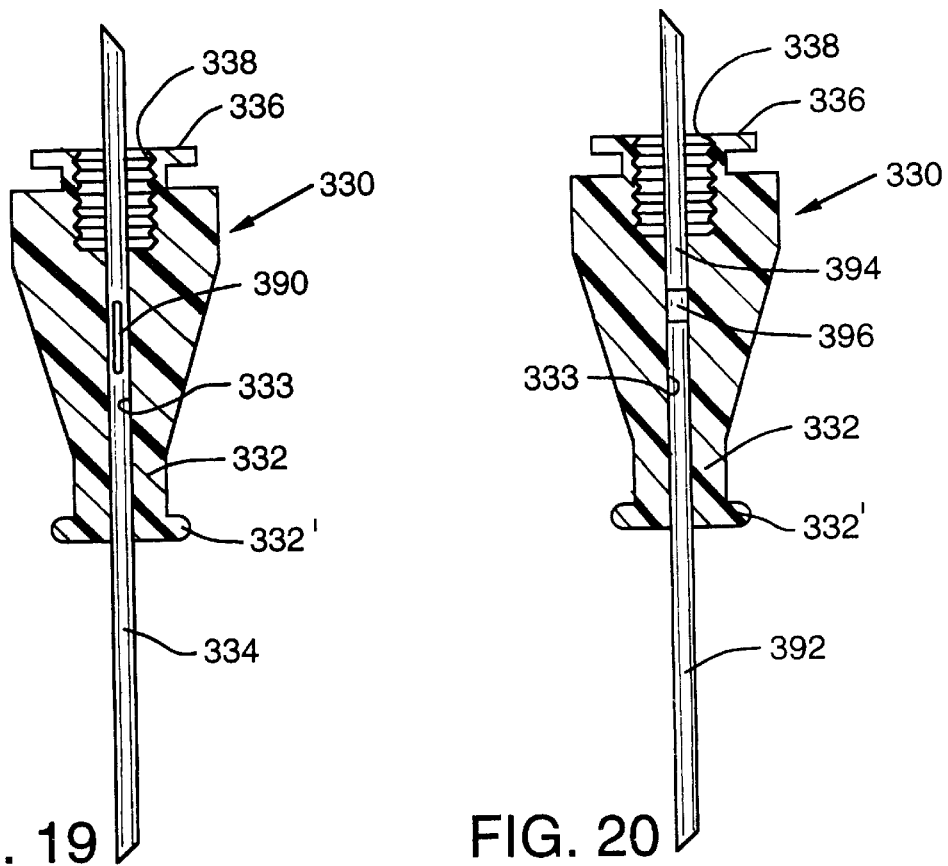
FIG. 19
FIG. 20

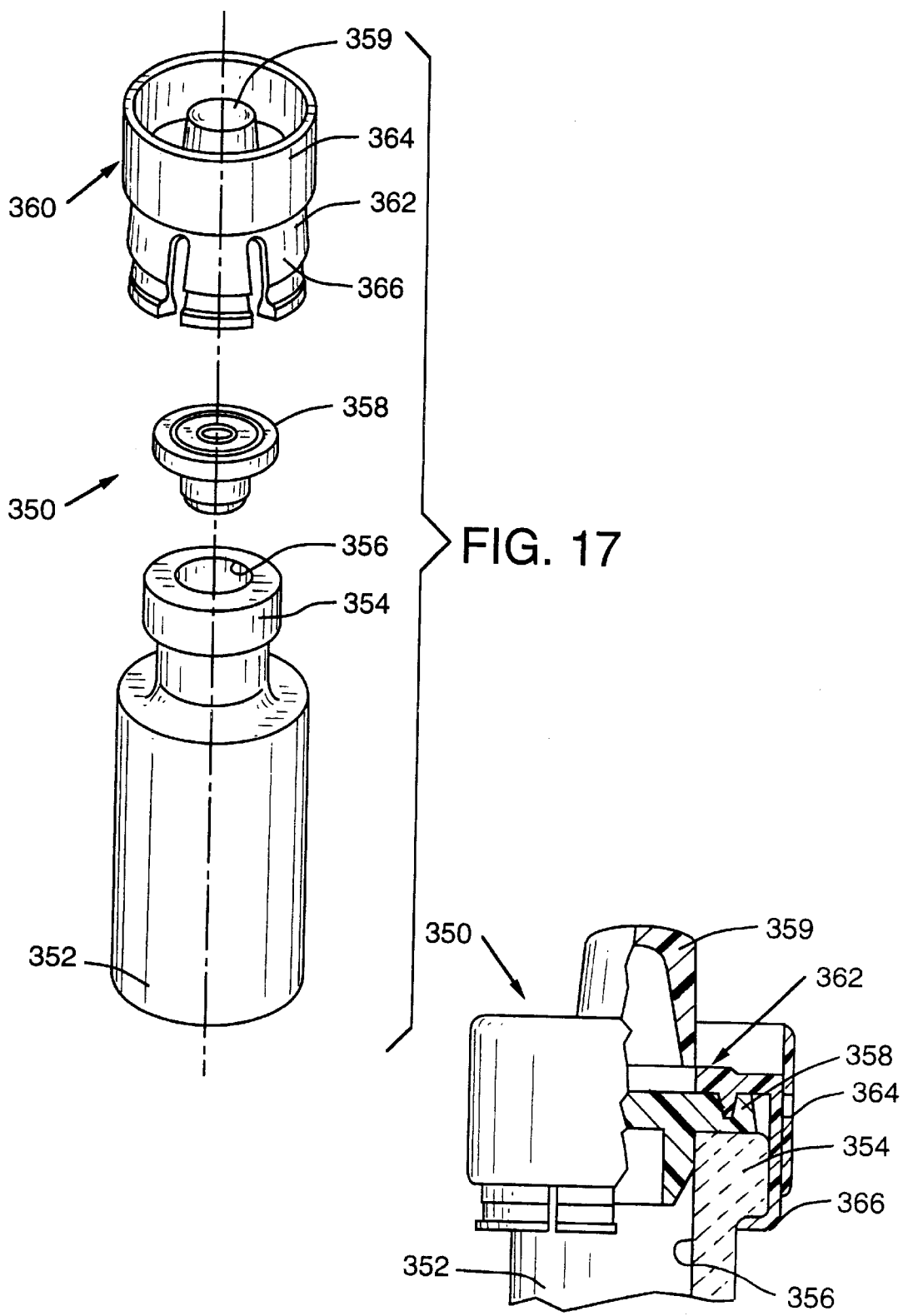

HYPODERMIC INJECTOR SYSTEM AND METHOD FOR MAINTAINING THE STERILITY THEREOF PRIOR TO USE

This is a divisional of application Ser. No. 08/661,260 filed on Jun. 10, 1996, now U.S. Pat. No. 5,718,690.

BACKGROUND OF THE INVENTION

1. Field of the Invention

The present invention relates to medical syringes and, more particularly, is directed to syringe systems adapted for use in connection with pre-filled medicament cartridges and methods for maintaining the sterility of such systems prior to use.

2. Description of the Invention Background

Hypodermic syringes are used for a variety of injection procedures including the delivery of medicinal drugs to a recipient. A typical hypodermic syringe arrangement may include a hollow syringe body that has a double-ended needle or cannula attached to one end of the tube. One end of the cannula usually protrudes from the syringe body for insertion into a patient or suitable port and is protected prior to use by a removable sheath. The other end of the cannula extends into the hollow syringe body for engagement with a cartridge that has been pre-filled with medicament.

The cartridge typically comprises a glass tube that is sealed at one end with a pierceable membrane usually fabricated from rubber. The other end of the cartridge is sealed by a plunger member that is slidably mounted within the cartridge tube. The cartridge is inserted into the open end of the syringe body until the inwardly protruding cannula pierces through the rubber seal. A plunger rod is then inserted through the open end of the syringe body to engage the plunger located in the cartridge. The sheath is removed from the outer end of the cannula to enable it to be inserted into a patient or port. The medicament is discharged through the cannula by axially pushing the plunger rod and plunger towards the cannula. In instances wherein it is desirable to use the syringe as an aspirator, the plunger rod is fastened to the plunger to enable the plunger to be pulled towards the rear end of the cartridge. Such movement of the plunger will cause body fluids to be drawn into the cartridge through the cannula.

A great majority of syringes used today are disposable to prevent the spread of infectious diseases from the reuse of contaminated syringes. The syringe components (i.e., the syringe body/cannula assembly, cannula sheath and plunger rod) are sterilized and packaged in an airtight sterile package for shipment to the end user. Because the syringes are discarded after a single use, it is desirable to minimize their cost.

Over the years, syringe manufacturers have developed various innovative syringe designs that utilize relatively low cost plastics in an effort to make the use of disposable syringes a safe and economically viable alternative to using reusable syringes that must be re-sterilized prior to each use. For example, U.S. Pat. No. 2,693,803 to Ogle discloses a disposable pre-filled syringe which has a plunger rod that functions as a needle sheath prior to use. The syringe body houses the medicament and is sealed on one end by a plunger and the plunger rod serves to encase the end of the needle when it is pressed onto the front of the syringe body. However, these disposable syringe arrangements are ill-suited for use with separate pre-filled medicament cartridges which may be supplied by a host of different suppliers. Also, because the plunger rod is only pressed onto the front of the syringe, it is susceptible of being jarred loose during shipping which could compromise the syringe's sterility. Similar syringe designs are disclosed in U.S. Pat. No. 2,616,420 to Hart, U.S. Pat. No. 2,662,740 to Hickey, U.S. Pat. No. 2,880,723 to Adams, U.S. Pat. No. 3,375,825 to Keller, U.S. Pat. No. 3,534,734 to Budreck and U.S. Pat. No. 3,783,997 to Brown.

Another syringe arrangement is disclosed in U.S. Pat. No. 2,728,341 to Roehr. That arrangement employs a hollow plunger rod for storing a detachable hub mounted cannula. A sterile stopper must be inserted in the open end of the plunger rod to maintain the sterility of the cannula prior to use. While this syringe arrangement is constructed for use with a pre-filled cartridge, it requires the application of a sterile stopper to the open end of the plunger rod to maintain the sterility of the cannula prior to use.

Other syringes that are adapted for use with pre-filled cartridges are disclosed in U.S. Pat. No. 2,826,195 to Ashkenaz, U.S. Pat. No. 4,808,169 to Haber et al. and Patent Cooperation Treaty Application Serial No. PCT/US88/03316 to Habley Medical Technology Corporation. In each of those syringe designs, the plunger rod is adapted to alternatively serve as a needle sheath prior to use. However, to maintain the sterility of these syringes prior to use, they must be packaged in airtight sterile packages.

In addition, medications adapted to be administered by means of injection through a needle or cannula are designed for introduction into a patient's system in a specific manner. Certain medications must not be injected into a patient's vein or artery. Instead, some types of medications are adapted to be injected intramuscularly or subcutaneously. When medications are administered subcutaneously or intramuscularly, the injection device is typically aspirated after the cannula has been injected into the patient. During such aspiration, the user observes the rear end of the cannula through the transparent syringe barrel. If the forward point of the cannula has penetrated a vein or artery, blood will immediately appear in that area. With many hypodermic devices and medications, the foregoing procedure presents little or no problems with detecting the presence of blood. However, with certain medications such as those comprising translucent or opaque medicaments, visual detection of blood presents somewhat of a problem or at least an inconvenience since an excessive amount of blood must be withdrawn through the cannula before it becomes detectable. This problem is also commonly encountered with the syringe designs discussed above.

Thus, all of the above-mentioned syringe designs have various shortcomings. While some of those syringes do not have to be packaged in airtight sterile packages to maintain their sterility prior to use, they are ill-suited for use with separate cartridges that are pre-filled with medicament. Also, while some of the above-mentioned cartridges are specifically adapted for use in connection with separate pre-filled cartridges, they must be packed in sterile airtight packages prior to use to prevent them from becoming contaminated. Moreover, while some of the prior syringes can be used for aspiration purposes, they lack means for quickly detecting the presence of blood during aspiration.

Accordingly, there is a need for a syringe system that is adapted for use in connection with separate pre-filled medicament cartridges that do not have to be packaged in airtight packages to maintain their sterility prior to use.

There is a further need for a syringe system with the above-mentioned attributes that can be easily adapted for use in connection with a variety of different ports.

There is yet another need for a syringe that can be used for aspiration purposes that is equipped with means or quickly detecting the presence of blood during aspiration.

SUMMARY OF THE INVENTION

In accordance with a particular preferred form of the present invention, there is provided a hypodermic syringe for use in connection with a pre-filled medicament cartridge that is sealed on one end by a pierceable seal and at the other end by an axially movable plunger. In a preferred form, the syringe comprises a sterilizable syringe body that has a distal end, a hollow interior and an open proximal end. The syringe also includes a sterilizable double-ended cannula that is attached to the distal end of the syringe body such that one end protrudes from the distal end for insertion into a receiving body. The other end of the cannula protrudes into the hollow interior for piercing the pierceable seal in a pre-filled medicament cartridge inserted into the syringe body. The syringe also comprises a sterilizable plunger rod that has a first end constructed for removable attachment to the distal end of the syringe body to create a first seal therebetween. The first end also has an axial cavity for encasing the portion of the cannula that protrudes into the hollow interior. A sheath member is removably attachable to the distal end of the syringe body and serves to encase the outwardly protruding portion of the cannula. A second seal is created between the sheath member and the distal end of the syringe body such that after the syringe body, cannula and plunger rod have been sterilized and the plunger rod has been attached to the distal end of the syringe body to establish the first seal therebetween, the first and second seals maintain the sterility of the cannula prior to use. A preferred form of the present invention may also include blood detection apparatus for quickly detecting the presence of blood passing through the cannula during aspiration.

Accordingly, the present invention provides solutions to the aforementioned problems associated with prior syringe designs by providing a syringe that does not need to be packaged in an airtight container prior to use to maintain the sterility of the syringe components. Moreover, the present invention provides a means for detecting the presence of blood in the portion of the syringe supporting the cannula during aspiration. Thus, the user can easily detect the presence of blood during aspiration even when opaque medicament is used. While these unique and novel aspects of the present invention solve many problems encountered when utilizing prior syringe system arrangements, the skilled artisan will appreciate that these and other details, objects and advantages will become apparent as the following detailed description of the present preferred embodiments proceeds.

BRIEF DESCRIPTION OF THE DRAWINGS

In the accompanying drawings, there are shown present preferred embodiments of the invention wherein like reference numerals are employed to designate like parts and wherein:

FIG. 15 is an end view of the syringe body of FIGS. 12–14;

FIG. 16 is an end view of a preferred hub assembly of the syringe depicted in FIGS. 12–15;

FIG. 17 is an exploded assembly view of another cartridge adapted for use with the syringe systems of the present invention;

FIG. 18 is an assembly view of the cartridge of FIG. 17 showing portions of elements in cross-section;

FIG. 19 is a cross-sectional elevational view of the hub assembly of FIG. 16; and FIG. 20 is a cross-sectional elevational view of another preferred hub assembly of the present invention.

DETAILED DESCRIPTION OF THE PREFERRED EMBODIMENTS

Figure 1:
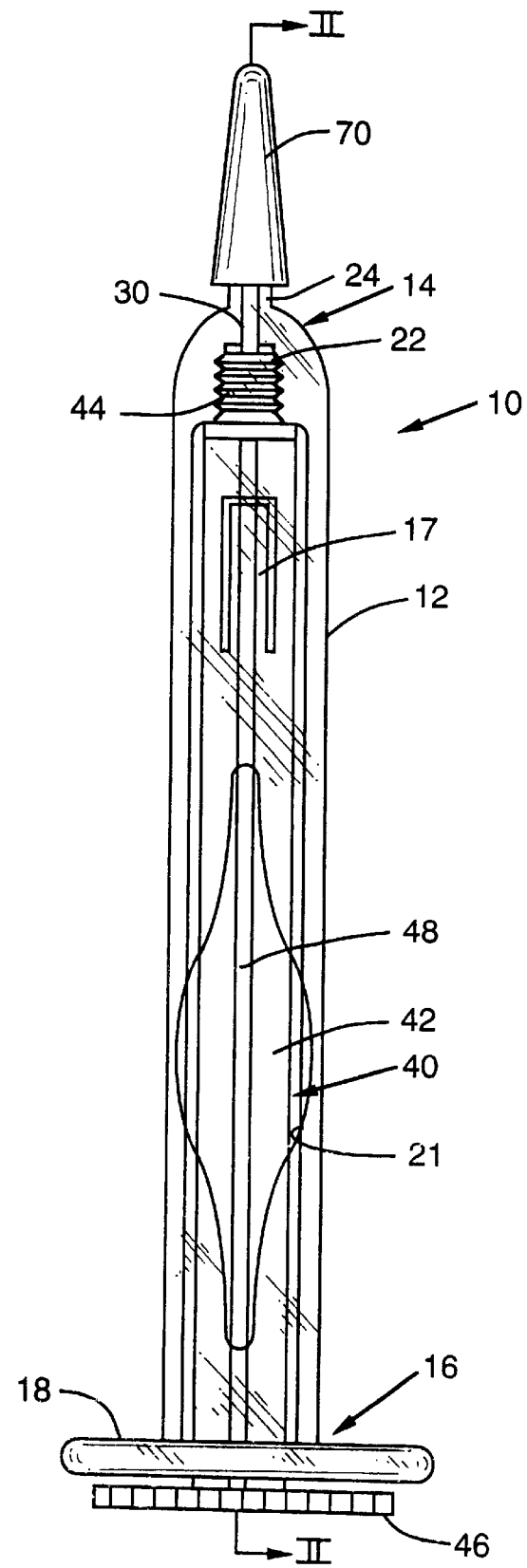
FIG. 1 is an assembly view of a preferred syringe assembly of the present invention prior to use with the plunger member attached to the syringe body.

Referring now to the drawings for the purposes of illustrating present preferred embodiments of the invention only and not for purposes of limiting the same, the Figures show a syringe assembly generally designated as 10. More particularly and with reference to FIGS. 1 and 2, there is shown a syringe assembly 10 that includes a hollow syringe body 12 that is preferably molded from substantially transparent polyethylene material that is capable of being sterilized utilizing known sterilization methods. However, the skilled artisan will of course appreciate that the syringe body 12 may be fabricated from other suitable materials that are capable of being sterilized.

Figure 2:
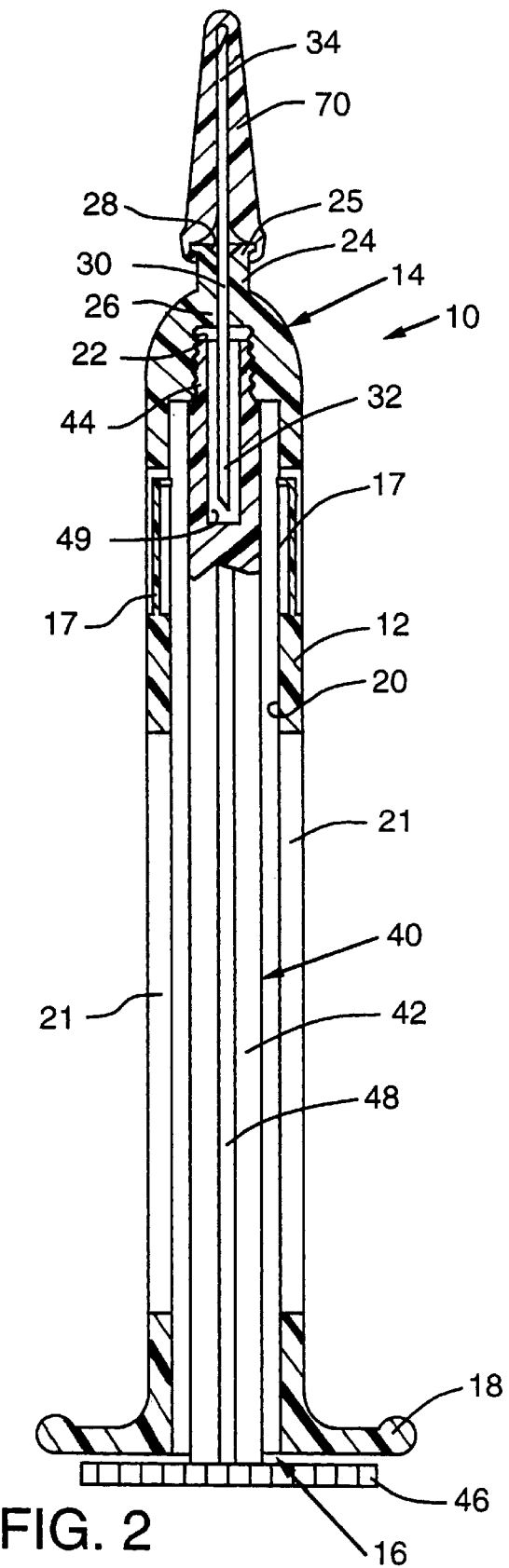
FIG. 2 is a cross-sectional view of the preferred syringe assembly of FIG. 1 taken along line II—II in FIG. 1.

As can be seen in FIGS. 1 and 2, the hollow syringe body 12 preferably has a tapered distal end 14 and an open proximal end 16. A flange member 18 is formed on the proximal end 16 to enable a user to grip and operate the syringe assembly 10 during use. The hollow syringe body has an axial cavity 20 that is sized to receive a pre-filled medicament cartridge 50. See FIG. 3. Two opposing openings 21 are also preferably provided in the syringe body 12 to enable the user to grip the sides of the cartridge 50 to assist with its insertion into the syringe body 12.

In a preferred embodiment, the distal end 14 of the syringe body 12 is formed with an outwardly protruding hub 24 for supporting a double-ended cannula 30. After a syringe body 12 is molded, a threaded counterbore 22 and a cannula-receiving passage 26 are preferably drilled into the distal end 14 in coaxial alignment with each other as shown in FIG. 2. When installed, cannula 30 has a first end 32 that axially protrudes through threaded counterbore 22 and into axial cavity 20 of syringe body 12. See FIG. 2. The second end 34 of cannula 30 is adapted for insertion into a patient or suitable port. Preferably, the double-ended cannula 30 is inserted into the cannula-receiving passage 26 and affixed in position with a suitable commercially available adhesive.

The syringe assembly 10 also includes a plunger rod 40 that is also preferably molded from polyethylene; however, plunger rod 40 may be fabricated from other suitable materials that are capable of being sterilized. Plunger rod 40 preferably has an axial body 42 and an attachment portion 44 formed on one end and an actuation plate 46 formed on the other end. Actuation plate 46 is adapted to be engaged by a user's finger or thumb to force the plunger rod 40 into the cartridge 50 or to withdraw it therefrom. Preferably, axial body 42 is formed with a plurality of (preferably four) axially extending support ribs 48.

The attachment portion 44 of plunger rod 40 is formed to threadably engage the threaded counterbore 22 in the distal end 14 of the syringe body 12. In addition, an axial cannula-receiving cavity 49 is provided in the attachment portion 48 of the plunger rod 40 as shown in FIG. 2 for selectively receiving end 32 of cannula 30 when the plunger rod 40 is attached to the distal end 14 of the syringe body 12. Also in this embodiment, a removable sheath member 70 is provided for encasing the second end 34 of the cannula 30 prior to use. Preferably, the sheath member 70 is molded from a suitable thermoplastic material and is adapted to removably engage a rib 25 formed on the end of hub 24. See FIG. 2.

After the syringe body 12, the plunger rod 40 and the sheath 70 have been fabricated, they are sterilized utilizing known sterilization methods. Thereafter, they are assembled as shown in FIG. 2. In the alternative, the plunger rod 40 and syringe body can be assembled as shown in FIGS. 1 and 2 and sterilized as a unit. In either case, the sterile sheath 70 is placed over the end 34 of the cannula 30 and snapped over the rib 25 on the hub 24 to retain the sheath 70 in position during shipping and storage of the syringe 10. The skilled artisan will appreciate that the threaded connection between the plunger rod 40 and the distal end 14 of the syringe body 12 create a tortuous path between those two components which retards the passage of bioburden between those components. Other mechanical attachment methods could also be employed to attach the plunger rod 40 to the distal end 14 of the syringe body 12 such that, after sterilization, the passage of bioburden therebetween. The skilled artisan will appreciate that after the syringe assembly is assembled as shown in FIG. 2, the plunger rod 40 and the sheath 70 cooperate to maintain the sterility of the cannula 30 prior to use. Thus, there is no need to package the syringe assembly 10 in an airtight/sterile package to maintain its sterility prior to use.

Figure 3:
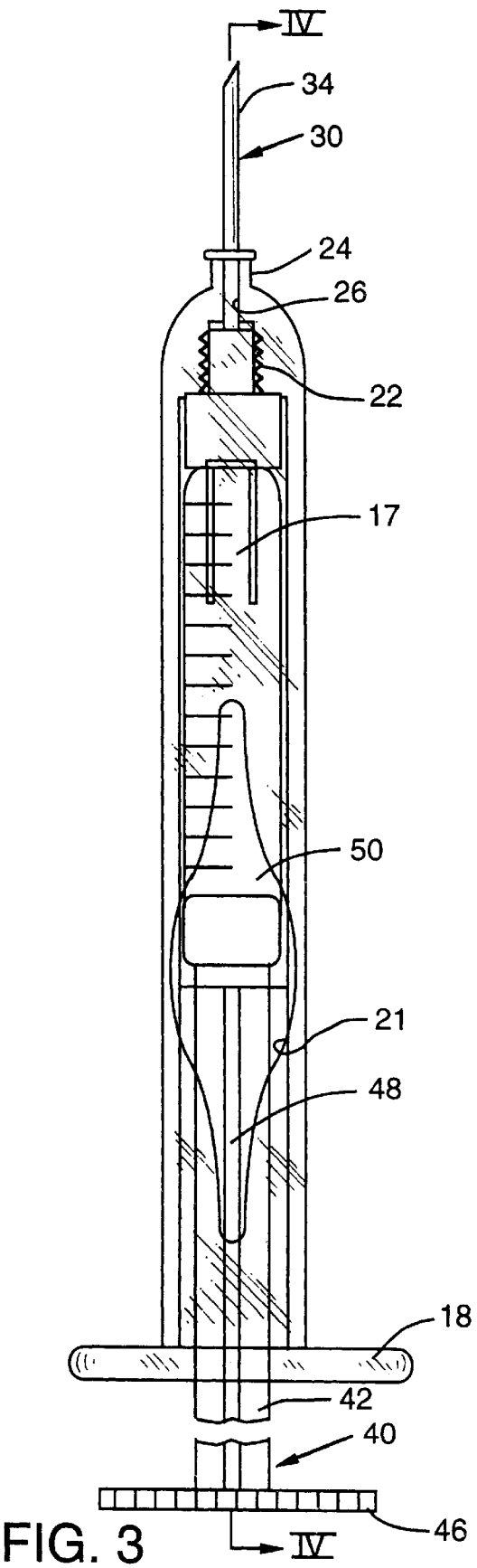
FIG. 3 is a view of the preferred syringe assembly of FIGS. 1 and 2 supporting a pre-filled medicament cartridge.

As can be seen in FIGS. 1 and 3, the present syringe assembly 10 is adapted for use in connection with a conventional cartridge 50 that is pre-filled with medicament. An exemplary cartridge 50 is shown in FIG. 5. As can be seen in that Figure, the cartridge 50 includes a hollow glass tube portion 52 that is formed with a hub 54. A passage 56 is provided through the hub 54 that is adapted to receive a rubber stopper 58. Rubber stopper 58 preferably has an outwardly extending port 59 that is adapted to receive a cannula. Stopper 58 serves to seal the passage 56 and is adapted to be pierced by a cannula that is inserted through port 59. Stopper 58 is retained in position by a plastic collar assembly 60. In a preferred form, collar assembly 60 includes a plastic sheath portion 62 that is inserted over the port 59 of stopper 58. Sheath portion 62 includes a series of attachment arms 66 that are adapted to engage hub 54. A ring member 64 is axially inserted over the sheath 62 and serves to retain the attachment arms 66 in engagement with the hub 54. After the tube 52 of the cartridge has been filled with medicament, a sterile plunger 68 is inserted into the open end of the tube 52 to retain the medicament within the tube 52. See FIG. 4. Typically, plunger 68 is provided with a threaded bore 69 or other suitable means for attaching the plunger rod 40 to the plunger. The cartridge 50 is sterilized utilizing known methods prior to being filled with medicament. Thereafter, the cartridge 50 can be shipped to the end user.

Figure 4:
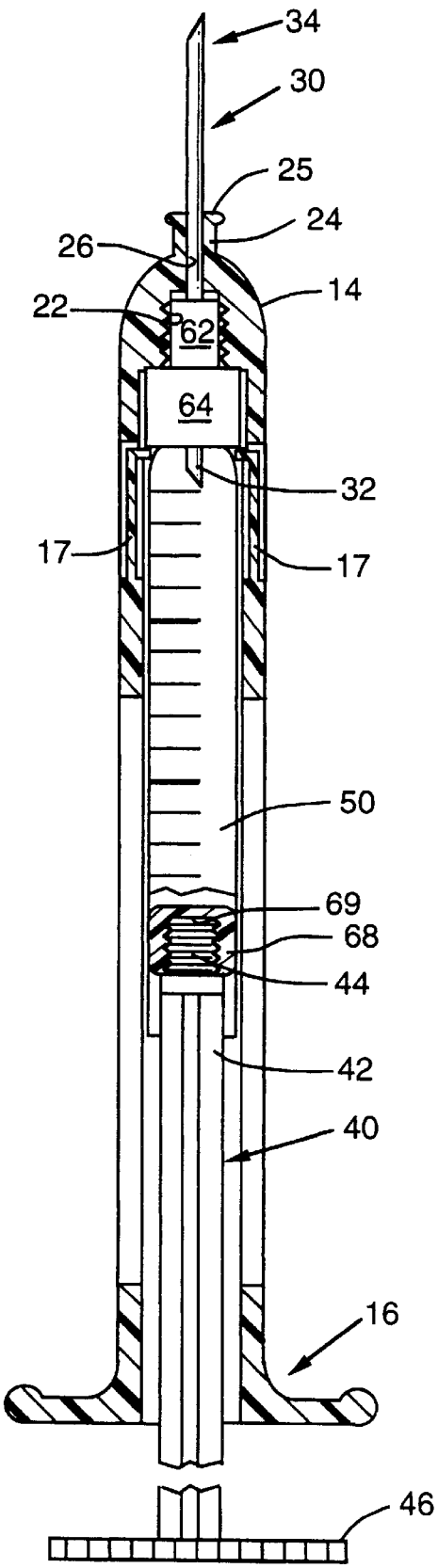
FIG. 4 is a cross-sectional view of the syringe assembly of FIG. 3 with some of the elements thereof shown in full view for clarity.
Figure 5:
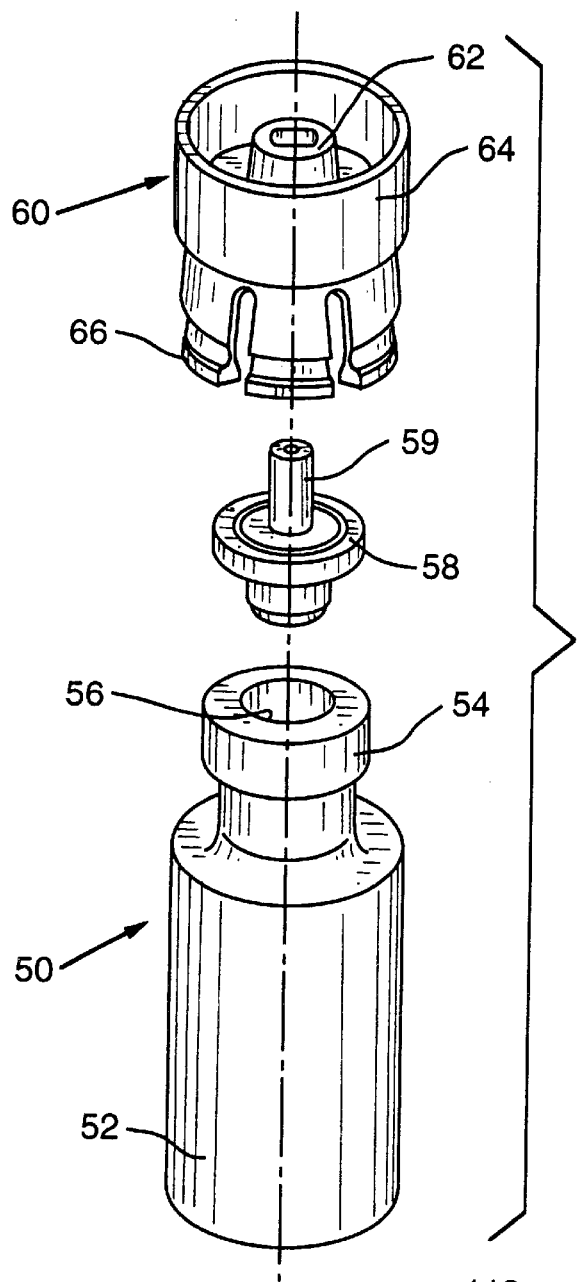
FIG. 5 is an exploded assembly view of a cartridge assembly adapted for use with the syringe systems of the present invention.

To use the syringe 10 of the present invention, the plunger rod 40 is detached from the distal end 14 of the syringe body 12 and a cartridge 50 is inserted into the axial passageway 20 until the cartridge 50 is seated as shown in FIGS. 3 and 4. The reader will appreciate that when the cartridge 50 is seated in the syringe body 12, the end 32 of the double ended cannula 30 pierces through the rubber stopper 58 in the cartridge 50. Thereafter, the attachment end 44 of the plunger rod 40 is threaded into the threaded bore 69 in the plunger 68. The sheath 70 is then detached from the hub 24 to enable the cannula 30 to be inserted into a patient or suitable port. To inject the medicament through the cannula 30, the user axially advances the plunger 68 towards the distal end 14 of the syringe body 12 by pressing the plunger rod 40 in that direction.

Figure 6:
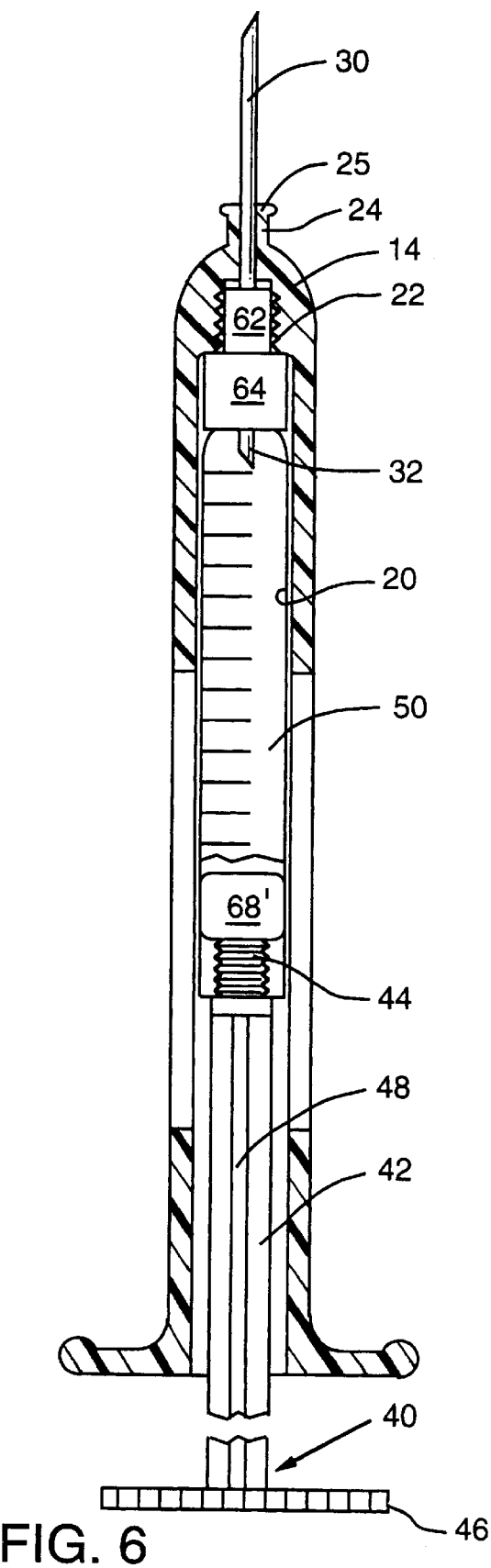
FIG. 6 is a cross-sectional view of another preferred syringe assembly of the present invention supporting a pre-filled medicament cartridge.

The skilled artisan will appreciate that the above-mentioned embodiment can be used for aspiration purposes. That is, by withdrawing the plunger rod 40 and plunger 68 away from the cannula 30, body fluids are drawn into the cartridge tube 52 through the cannula 30. To retain the cartridge 50 in position while aspirating, the syringe body 12 is preferably provided with at least one, and preferably two, retaining tabs 17. As can be seen in FIGS. 2 and 4, retaining tabs 17 have a reduced cross-sectional area and are capable of flexing outward when the cartridge 50 is inserted into the syringe body 12. However, after the cartridge 50 has been seated in the syringe body 12, the retaining tabs 17 serve to engage the collar assembly 60 on the cartridge 50 to prevent the cartridge 50 from being pulled out of the syringe body 12 during use. See FIG. 4. It will be further appreciated, however, in instances where the ability to aspirate is not required or desirable, the threaded bore 69 or other attachment arrangement for attaching the plunger rod 40 to the plunger 68 can be omitted. See FIG. 6. In that arrangement, the plunger rod 40 is used to bear upon the plunger 68 to axially advance the plunger 68 towards the cannula 30.

Figure 7:
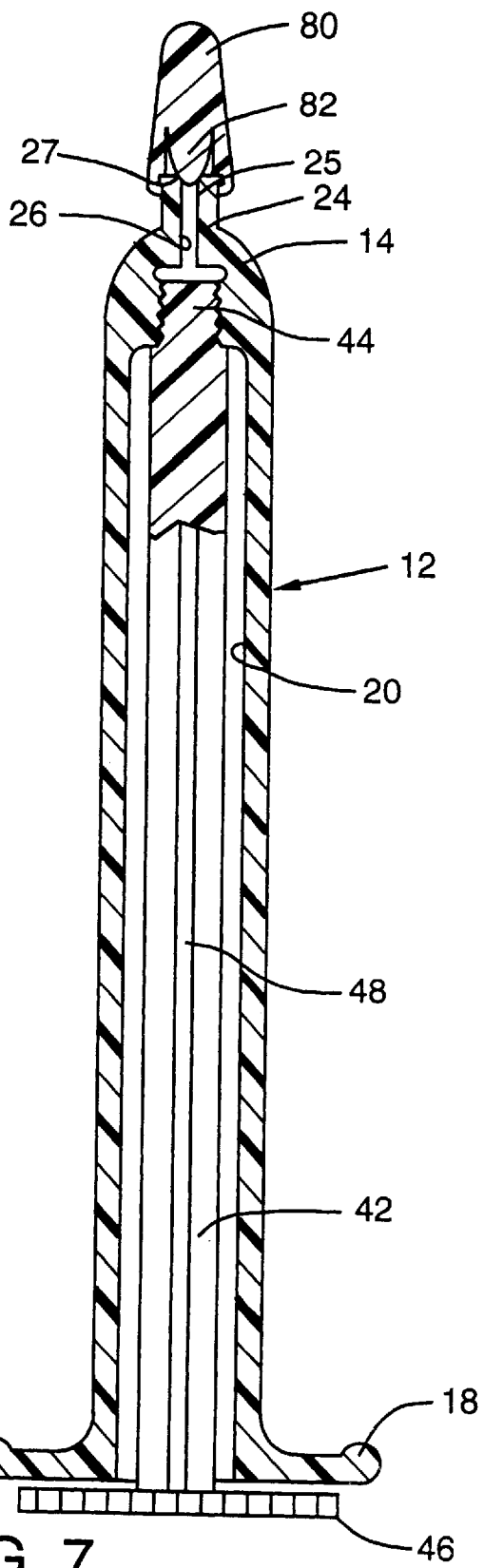
FIG. 7 is a cross-sectional view of another preferred syringe assembly of the present invention prior to use with the plunger member attached to the syringe body.

The construction of the subject invention is also well-adapted for providing a sterile syringe body to an end user that desires to attach a cannula to the syringe body just prior to use. As can be seen in FIG. 7, such embodiment includes a stopper 80 that is adapted to engage the rib 25 of the hub 24. Preferably the cannula-receiving passage 26 has a tapered end 27 that is adapted to receive an inwardly extending conical-shaped seal portion 82 of stopper 80.

Such stopper 80, in combination with the attachment of the plunger rod 40 to the distal end 14 of the syringe body, serves to maintain the sterility of the cannula-receiving passage 26 prior to use.

Figure 9:
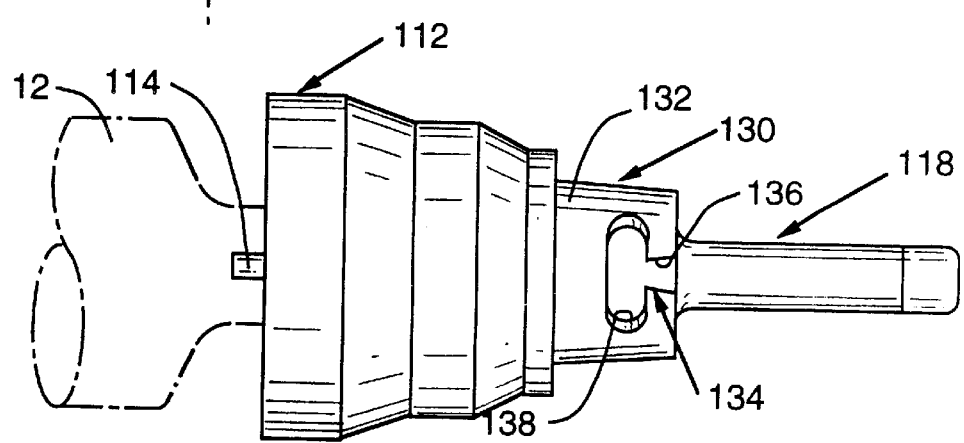
FIG. 9 is a view of a preferred syringe assembly of FIG. 8.
Figure 8:
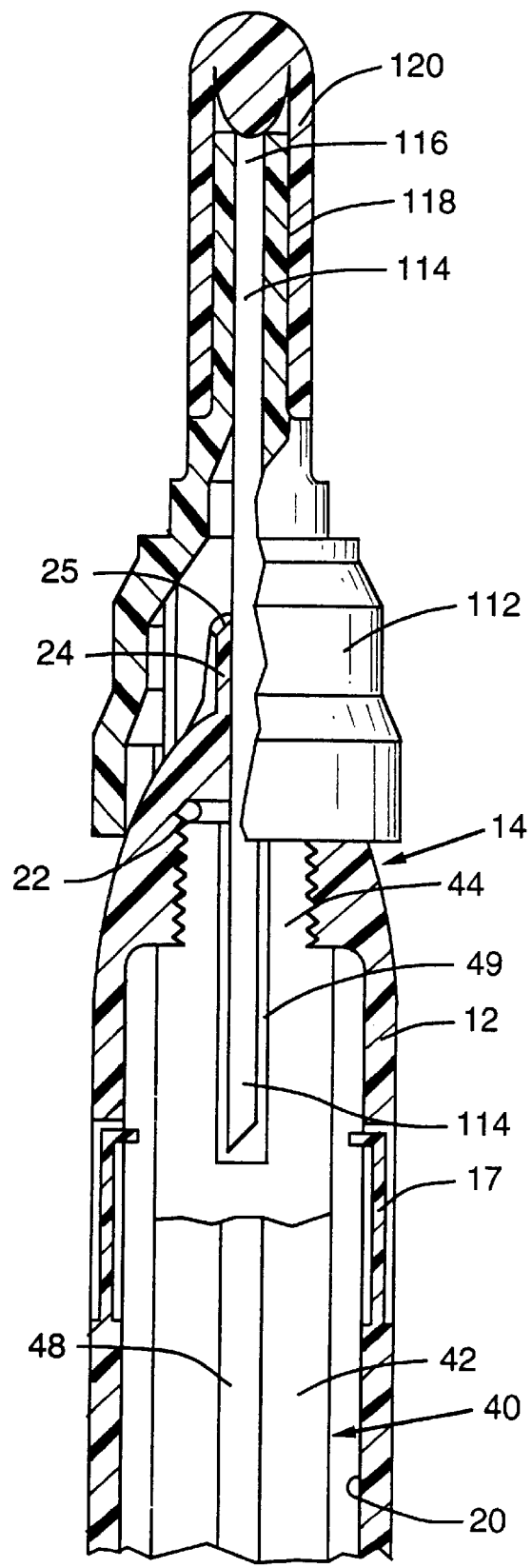
FIG. 8 is a partial cross-sectional assembly view of another preferred syringe assembly of the present invention prior to use.

The present invention is also well-adapted for use in connection with syringe adaptor systems of the type disclosed in the copending U.S. patent application Ser. No. 08/481,080, filed Jun. 7, 1995, the disclosure of which is herein incorporated by reference. For example, as shown in FIGS. 8 and 9, the syringe hub 24 can be attached to a fitting member 112 that is pressed onto the hub 24 and retained in position by commercially available adhesive. The skilled artisan will appreciate that the fitting member 112 includes a cannula 114 that extends into the axial body 12 of the syringe 10 and is adapted to pierce the pierceable stopper in a cartridge 50 received within the syringe body 12 See FIG. 9. The outer end 116 of the cannula 114 extends through a nose portion 118 of the fitting 112 that is sized for insertion into corresponding intravenous ports, etc. Prior to use, however, the plunger rod 140 is attached to the distal end 14 of the syringe body 12 such that the inwardly protruding portion of cannula 114 is received within cavity 49 in plunger rod 40. The outer end 116 of the cannula 114 can be sealed by a removable sheath 120 as shown in FIG. 8. The reader will again appreciate that the sealing attachment of the plunger rod 40 to the syringe body 12, in combination with the seal achieved between the nose 118 and the sheath 120, serves to preserve the sterility of the cannula 114 prior to use.

Figure 10:
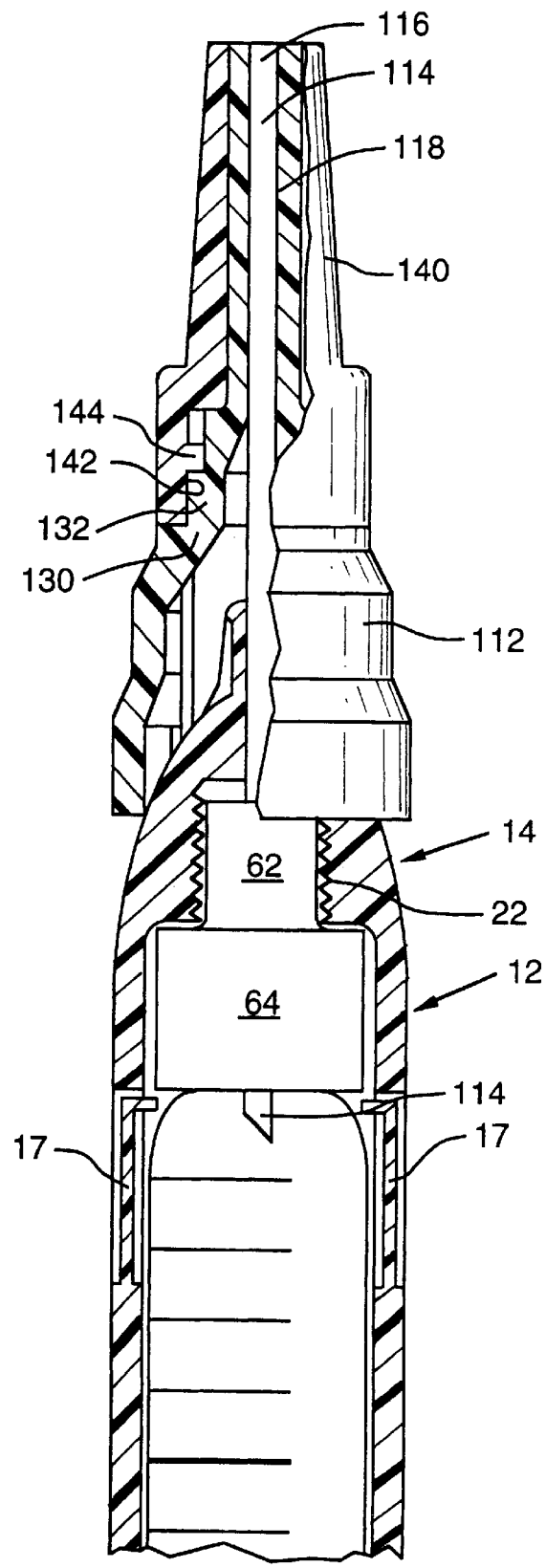
FIG. 10 is a partial cross-sectional assembly view of the syringe assembly of FIG. 8 supporting a pre-filled medicament cartridge and having an adaptor member attached thereto.

Referring to FIGS. 9 and 10, the syringe fitting 112 is formed with a fitting mounting portion 130 that preferably has a tapered side wall 132 that is adapted to slidably engage a corresponding tapered interior wall 142 of a port formed in a removable adaptor 140 to create a fluid-tight seal therebetween. To mechanically secure an adaptor 140 having an outer diameter/configuration that differs from the configuration the nose 118, two diametrically opposed T-shaped slots 134 are provided in the mounting portion 130. See FIG. 9. Each slot 134 has an axial portion 136 and a transverse portion 138 that are substantially arranged in the shape of a "T". It will be appreciated that the slot portions (136, 138) are sized to slidably receive therein inwardly-protruding pins 144 formed in an adaptor member 140. See FIG. 10. In a preferred embodiment, the slot portion 138 forms a radially extending pathway on the mounting member 130 of approximately seventy-six degrees. However, the portion 138 of a slot 134 may be formed in the mounting portion 130 such that it extends therearound any radial distance and it may even form a continuous passage that extends completely around the circumference of the mounting member 130.

To attach the adaptor 140 to the fitting 112, the adaptor 140 is brought into confronting relationship with the fitting 112 such that the pins 144 of the adaptor 140 are axially aligned with a corresponding slot portion 134 in the mounting portion 130 of the fitting 112. The adaptor 140 is then axially displaced on the fitting 112 until the pins 144 reach the slot portion 138. Thereafter, the adaptor is rotated in a clockwise or counterclockwise direction relative to the fitting 112 to cause the pins 144 to be advanced to positions in the slot portion 168 such that they are no longer axially aligned with their corresponding slot portions 136 to thereby retain the adaptor 140 on the fitting 112. It will be appreciated that the outer wall of the mounting portion 130 is tapered in conformance with a tapered inner wall of the adaptor 140 to achieve a fluid-tight seal therebetween.

Figure 11:
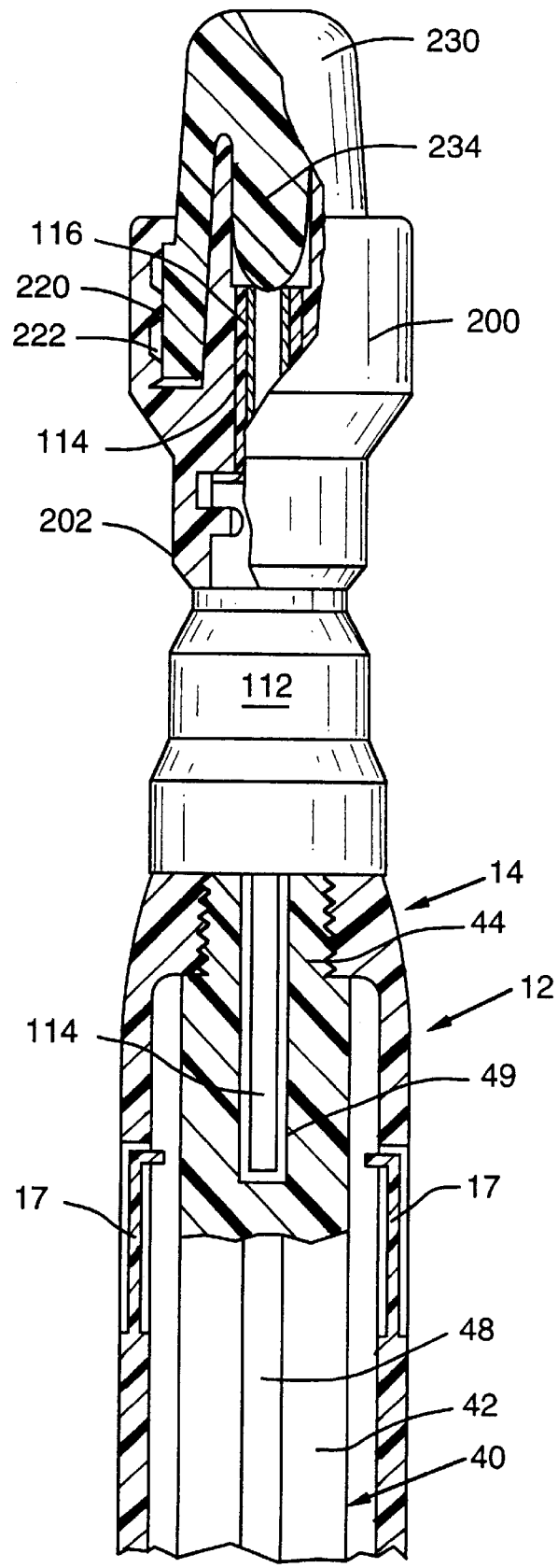
FIG. 11 is a partial cross-sectional assembly view of a preferred syringe assembly of the present invention having a luer lock adaptor attached thereto prior to use.

FIG. 11 depicts another adaptor 200 that can be used with the fitting 112. Adaptor 200, in a preferred form comprises a luer lock member that has an attachment portion 202 that is attachable to the mounting portion 130 of the fitting 112 in the manner described above. As can be seen in FIG. 11, a preferred adaptor 200 also has a locking skirt 220 that has a series of internal threads 222 for attaching the adaptor 200 to a corresponding port arrangement (not shown). Preferably, a protective cap 230 is provided with an inwardly protruding seal member that has a conical tip 234 adapted to sealingly engage the end 116 of the cannula 114. Thus, the protective cap 230, in combination with the attachment of the plunger rod 40 to the syringe body 12, serves to maintain the sterility of the cannula 114 prior to use.

Another preferred syringe assembly 310 of the present invention is depicted in FIGS. 12–16. The syringe assembly 310 includes a hollow syringe body 312 that is preferably fabricated from polyethylene that is capable of being sterilized utilizing known sterilization methods. However, other materials could also be successfully used to fabricate the body 312. The body 312 has a distal end 314 and an open proximal end 316. A flange member 318 is formed on the proximal end 316 to enable a user to grip and operate the syringe assembly 310 during use. An axial cavity 320 is provided in the syringe body 312 and, as will be discussed below, is sized to receive a pre-filled medicament cartridge of the type disclosed in U.S. Pat. No. 5,085,332, the disclosure of which is herein incorporated by reference.

Figure 12:
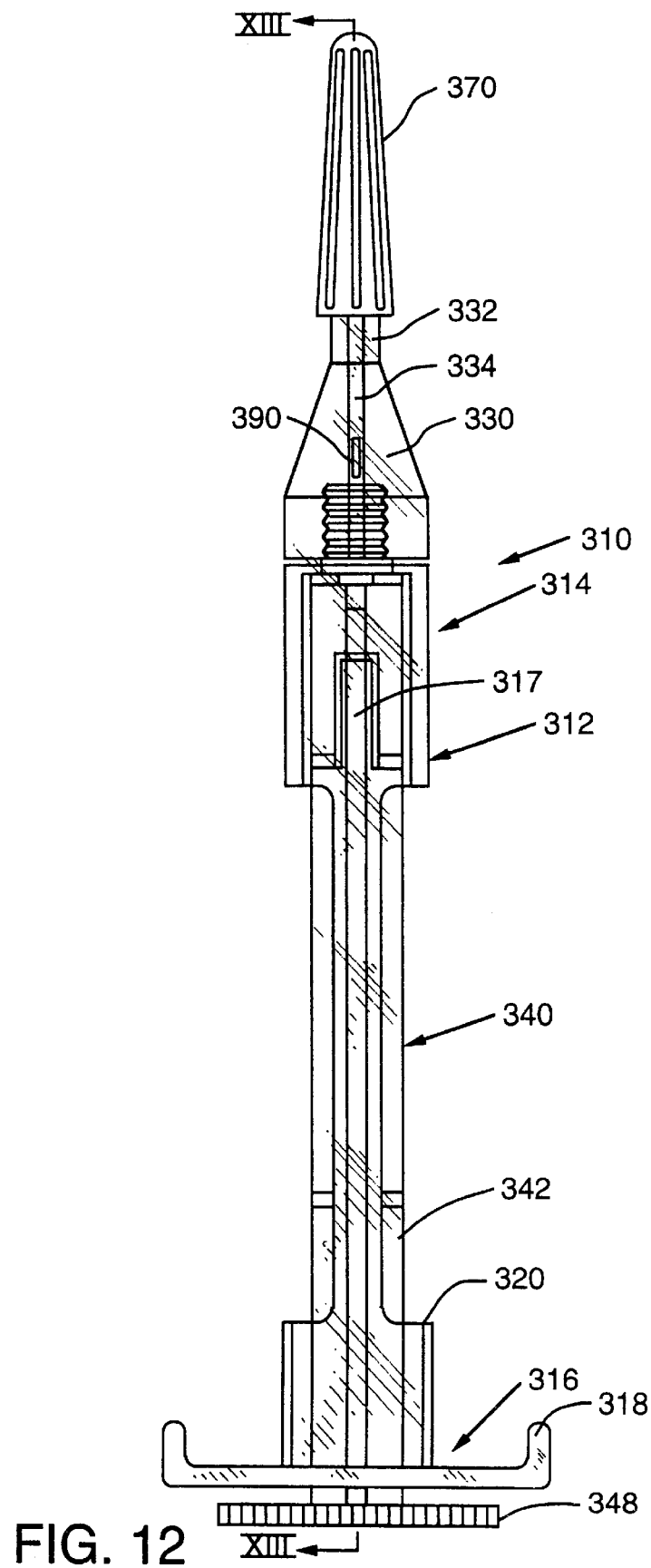
FIG. 12 is an assembly view of another preferred syringe assembly of the present invention prior to use with the plunger member attached to the syringe body.
Figure 13:
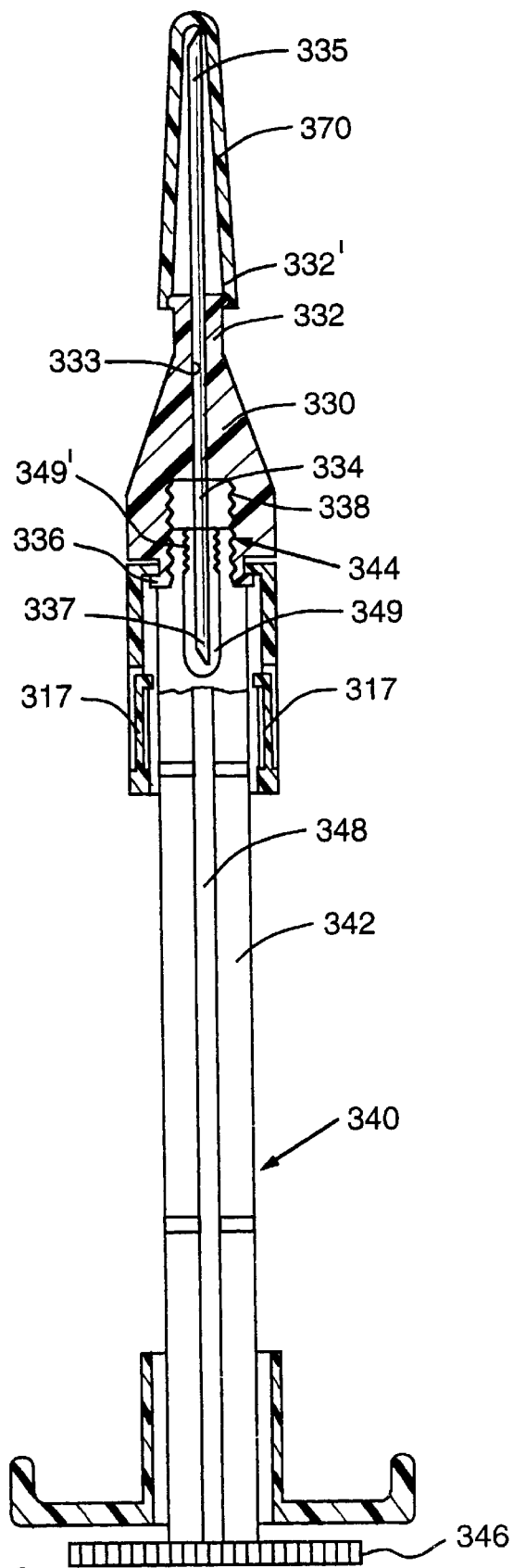
FIG. 13 is a cross-sectional view of the preferred syringe assembly of FIG. 12 taken along line XIII—XIII in FIG. 12.
Figure 14:
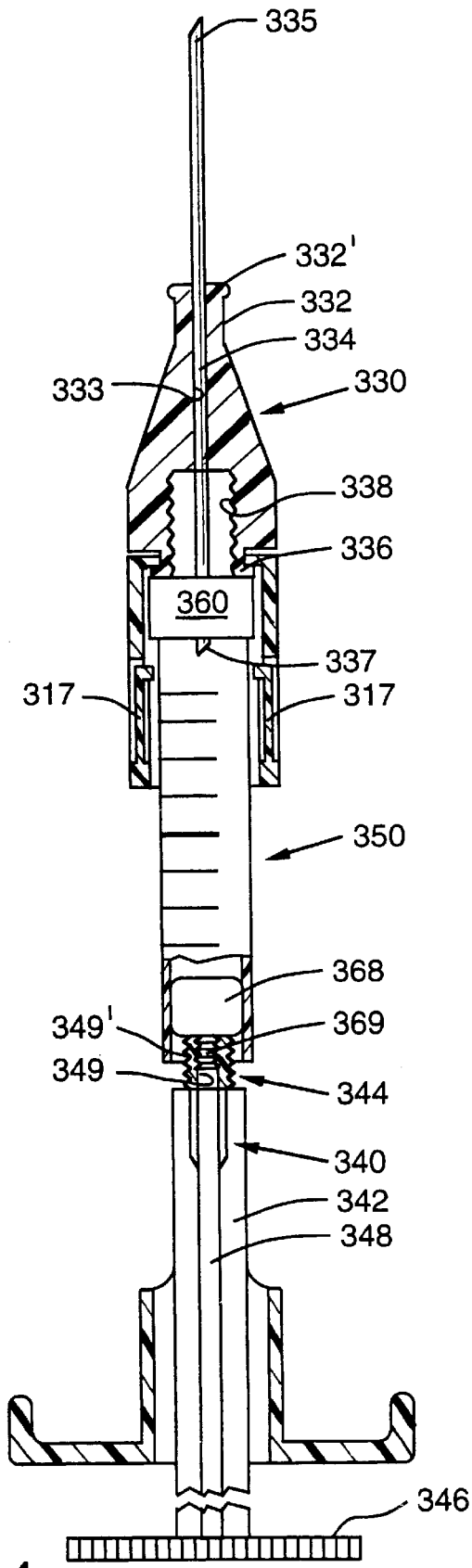
FIG. 14 is a view of the preferred syringe assembly of FIGS. 12 and 13 supporting a pre-filled medicament cartridge.

In this embodiment, the syringe assembly 310 also includes a detachable hub assembly 330. Hub assembly 330 is preferably configured as shown in FIGS. 12–14 and is preferably molded from transparent polyethylene. One end of the hub assembly 330 is preferably formed with an outwardly protruding hub 332 for supporting a double-ended cannula 334 and the other end of the hub assembly 330 has a fastening member 336 for removably attaching the hub assembly 330 to the distal end 314 of the syringe body 312. Fastening member 336 is preferably configured as shown in FIG. 16 and has a series of four connection tabs 336'. Fastening member 336 is adapted to be inserted through a correspondingly shaped aperture 315 in the distal end 314 of the syringe body 312. After the fastening member 336 has been inserted into the aperture 315, the hub assembly 330 is turned approximately forty-five degrees to cause the connection tabs 336 to be misaligned with the aperture 315 and thus affix the hub assembly 330 to the syringe body 312. See FIG. 13. The skilled artisan will appreciate, however, that the hub assembly 330 can be removably attached to the syringe body 312 by other suitable fastening arrangements (i.e., threads, bayonets, etc.).

An axial passage 333 is provided in hub assembly 330 for receiving the double-ended cannula 334. A threaded cavity 338 is also provided in the hub assembly 330. Cavity 338 is preferably coaxially aligned with axial passage 333 and extends through the fastening member 336. See FIG. 13. Double-ended cannula 334 is retained in axial passage 333 by conventional means (i.e., commercially available adhesive). The end 335 of the cannula 334 protrudes from one end of the hub 332 for insertion into a receiving body or port (not shown). The other end 337 of the cannula 334 protrudes into the axial cavity 320 in the syringe body 312 when the hub assembly 330 is attached to the syringe body 312.

The syringe assembly 310 also includes a plunger rod 340 that is also preferably molded from polyethylene; however, plunger rod 340 may be fabricated from other suitable materials that are capable of being sterilized. Plunger rod 340 preferably has an axial body 342 and an attachment portion 344 on one end and an actuation plate 346 on the other end. Actuation plate 346 is adapted to be easily engaged by a user's finger or thumb to force the plunger rod into the syringe body 312 or to withdraw it out of the syringe body 312. Preferably, axial body 342 is formed with a plurality of (preferably four) axially extending support ribs 348.

The attachment portion 344 of plunger rod 340 is preferably constructed to threadably engage the threaded cavity 338 in the hub assembly 330. See FIG. 13. In addition, an axial cannula-receiving cavity 349 is provided through the attachment portion 344 of the plunger rod 340 as shown in FIG. 13 for selectively encasing the end 337 of the cannula 334. Also in this embodiment, a removable sheath member 370 is provided for encasing the end 335 of the cannula 334 prior to use. Preferably, the sheath member 370 is molded from a suitable thermoplastic or rubber material and is adapted to removably engage a rib 332' formed on the end of hub 332. See FIG. 13.

After the syringe body 312, the hub assembly 330, the plunger rod 340 and the sheath 370 have been fabricated, they are sterilized utilizing known sterilization methods. Thereafter, they are assembled as shown in FIG. 13. In the alternative, the hub assembly 330, the syringe body 312 and the plunger rod 340 can be assembled and sterilized as a unit. In either case, the sterile sheath 370 is placed over the end of the cannula 334 and snapped over the rib 332' on the hub 332 to retain the sheath 370 in position during shipping and storage of the syringe 310. The plunger rod 340 is also axially inserted through the open proximal end 316 of the syringe body 312 and the attachment end 344 of the plunger rod 340 is threaded into the threaded cavity 338. The skilled artisan will appreciate that the threaded connection between the plunger rod 340 and the hub assembly 330 create a substantially tortuous path between those two components which retards the passage of bioburden therebetween. Other mechanical attachment methods could also be employed to attach the plunger rod 340 to the hub assembly 330 of the syringe body 312 such that after sterilization, the passage of bioburden between those two components is substantially prevented. The skilled artisan will appreciate that after the syringe assembly 310 is assembled as shown in FIG. 13, the plunger rod 340 and the sheath 370 cooperate to maintain the sterility of the cannula 334 prior to use. Thus, there is no need to package the syringe 310 an airtight/sterile package to maintain its sterility prior to use.

As can be seen in FIGS. 14, 17 and 18, the present syringe assembly 310 is adapted to be used in connection with a conventional cartridge 350 that is pre-filled with medicament. An exemplary cartridge 350 is shown in FIGS. 17 and 18 and is described in detail in U.S. Pat. No. 5,085,332. As can be seen in FIGS. 17 and 18, the cartridge 350 includes a hollow glass tube portion 352 that is formed with a hub 354. A passage 356 is provided through the hub 354 that is adapted to receive a rubber stopper 358. Stopper 358 serves to seal the passage 356 and is adapted to be pierced by a cannula 334. Stopper 358 is retained in position by a plastic collar assembly 360. In a preferred form, collar assembly 360 includes a plastic sheath portion 362 that is inserted over the hub 354 and includes a series of attachment arms 366 that are adapted to engage hub 354. A ring member 364 is axially inserted over the sheath 362 and serves to retain the attachment arms 366 in engagement with the hub 354. A cap 359 is attached to the sheath portion 362 by a plurality of frangible elements (not shown). In preparation for use, the cap 359 is removed from the sheath portion 362 hub thus exposing the rubber stopper 358. After the tube 352 of the cartridge has been filled with medicament, a sterile plunger 368 is inserted into the open end of the tube 352 to retain the medicament within the tube 352. See FIG. 14. Typically, plunger 368 is provided with a threaded sprue 369 or other suitable means for attaching the plunger rod 340 to the plunger. Threaded sprue 369 is adapted to threadably engage the threaded portion 349' of the axial cavity 349 in the end 344 of the plunger rod 340. See FIGS. 13 and 14. The cartridge 350 is sterilized utilizing known methods prior to being filled with medicament. Thereafter, the cartridge 350 is packaged for shipment to the end user.

To use this embodiment, the cap 359 is removed from the cartridge 350. The plunger rod 340 is removed from the syringe body 312 and the cartridge 350 is inserted into the axial passageway 320 until the cartridge 350 is seated as shown in FIG. 14. The reader will appreciate that when the cartridge 350 is seated in the syringe body 312, end 337 of the double ended cannula 334 pierces through the rubber stopper 358 in the cartridge 350. Thereafter, the attachment end 344 of the plunger rod 340 is threaded on the threaded sprue 369 of the plunger 368. The sheath 370 is then detached from the hub 324 to enable the end 335 of the cannula 334 to be inserted into a patient or suitable port. To inject the medicament through the cannula, the user axially pushes the plunger 368 towards the hub assembly 330 by advancing the plunger rod 40 in that direction.

The skilled artisan will appreciate that the above-mentioned embodiment can be used for aspiration purposes by withdrawing the plunger rod 340 and plunger 368 away from the cannula 334 to cause body fluids to be drawn into the cartridge 350 through the cannula 334. To retain the cartridge 350 in position while withdrawing the plunger 368, the syringe body 312 is preferably provided with at least one, and preferably two, retaining tabs 317. As can be seen in FIGS. 12 an 13, retaining tabs 317 have a reduced cross-sectional area and are capable of flexing outward when the cartridge 350 is inserted into the syringe body 312. However, after the cartridge 350 has been seated in the syringe body 312, the retaining tabs 317 engage the collar assembly 360 on the cartridge 350 to prevent the cartridge 350 from being pulled out of the syringe body 312. See FIG. 14.

In this embodiment, at least one and preferably two viewing ports 390 are machined into the cannula 334 for detecting the presence of blood in the cannula during aspiration. See FIGS. 12 and 19. The skilled artisan will appreciate that the viewing ports 390 are viewable through the transparent hub assembly 330 to enable the user to monitor the viewing ports 390 for the presence of blood during aspiration. In an alternate embodiment as shown in FIG. 20, the cannula is separated into two segments (392, 394) with a viewing window 396 provided between. It will be appreciated that the aspirated blood and/or body fluids will pass through the first cannula segment 392 and into the viewing window 396 to enable any blood passing through the viewing window 396 to be visually detected. Further aspiration causes the blood and/or body fluids to enter the second cannula segment 394 for eventual discharge into the cartridge 350. Those of ordinary skill in the art will appreciate that such blood detection arrangement can also be successfully used in other syringe body constructions.

Accordingly, the present invention provides solutions to the problems associated with prior syringe designs. In particular, the present invention enables the sterility of a cannula-receiving passage or a cannula in a syringe to be maintained prior to use without the necessity of packaging the syringe in an airtight package. In addition to the above-mentioned advantages, the present syringe design can be adapted for use in connection with a variety of different port arrangements and/or it can be used to perform subcutaneous injections. Moreover, the subject invention can also be used for aspiration purposes and is equipped with means for quickly detecting the presence of blood during aspiration. It will be further understood, however, that various changes in the details, materials and arrangements of parts which have been herein described and illustrated in order to explain the nature of the invention may be made by those skilled in the art within the principle and scope of the invention as expressed in the appended claims.

What is claimed is:

1. A syringe for use in connection with a pre-filled medicament cartridge that is sealed on one end by a pierceable seal and at the other end by an axially movable plunger, the syringe comprising:

a sterilizable hollow syringe body having a distal end and an open proximal end for inserting a pre-filled medicament cartridge therein, said distal end of said syringe body having a double-ended cannula attached thereto such that one end thereof protrudes therefrom for insertion into a receiving body and the other end thereof protrudes into said hollow interior for piercing the pierceable seal of said pre-filled medicament cartridge received therein;

a sterilizable plunger rod removably attachable to said distal end of said syringe body in a storage position prior to insertion of said pre-filled medicament cartridge therein wherein said plunger rod is substantially received within said syringe body and wherein said plunger rod encases said portion of said cannula protruding into said hollow interior and establishes a first sterility maintaining seal with said syringe body, said plunger rod being detachable from said syringe body to permit said pre-filled medicament cartridge to be inserted into said syringe body and configured for insertion into said pre-filled medicament cartridge for engagement with said plunger received therein; and a sterilizable sheath member removably attachable to said distal end of said syringe body, said sheath member having a first cavity therein for receiving said outwardly protruding portion of said cannula and having means for creating a second sterility maintaining seal with said distal end of said syringe body such that after said sheath, syringe body and plunger rod have been sterilized and said plunger rod and said sheath have been attached to said distal end to establish said first and second seals therebetween, said first and second seals maintain the sterility of said cannula.

2. The syringe of claim 1 wherein said plunger rod has first and second ends, said first end having a primary cavity for receiving said portion of said cannula protruding into said hollow interior and first attachment means that cooperates with a second attachment means in said distal end of said syringe body to create a tortuous path between said distal end and said first end of said plunger rod when said plunger rod is attached to said distal end in said storage position.

3. The syringe of claim 2 wherein said first attachment means comprises threads formed on said first end of said plunger rod and said second attachment means comprises a threaded socket in said distal end of said syringe body.

4. The syringe of claim 1 wherein said plunger has second attachment means formed therein adapted to engage said first attachment means on said plunger rod to permit said plunger rod to be selectively attached to said plunger and wherein said syringe body has means for retaining said pre-filled medicament cartridge therein.

5. The syringe of claim 4 further comprising means in syringe body for detecting blood passing through said cannula during aspiration.

6. The syringe of claim 5 wherein said blood detection means comprises at least one viewing port provided in said cannula and wherein at least a portion of said syringe body is substantially transparent to enable a user to view said viewing ports therethrough.

7. The syringe of claim 5 wherein said distal end of said syringe body is substantially transparent and wherein said cannula comprises a first cannula segment coaxially aligned in spaced-apart relationship with a second cannula segment in said distal end of said syringe body to define a viewing passage therebetween which can be viewed by a user through said transparent distal end.

8. A method for maintaining the sterility of a sterilized hypodermic syringe having a hollow body member adapted to receive therein a pre-filled medicament cartridge sealed on one end by a pierceable seal and on the other end by an axially movable plunger, comprising the steps of:

providing a sterilizable syringe body having a hollow interior for receiving said pre-filled medicament cartridge therein, said syringe body having an open proximal end and a distal end that has a sterilizable double-ended cannula attached thereto such that one end thereof protrudes from said distal end for insertion into a receiving body and the other end thereof protrudes into said hollow interior for piercing said pierceable seal in said pre-filled medicament cartridge received in said syringe body to permit said medicament to be discharged from said cartridge through said cannula;

providing a sterilizable plunger rod having a first end and a second end, said first end having attachment means formed thereon for removably attaching said first end of said plunger rod to said distal end of said syringe body to create a first seal therebetween prior to inserting said pre-filled medicament cartridge into said syringe body, said first end having an axial cavity therein for receiving said portion of said cannula protruding into said hollow interior, said attachment means also formed for attachment to said plunger in said pre-filled medicament cartridge after said plunger rod has been detached from said distal end of said syringe body and said pre-filled medicament cartridge has been inserted into said hollow interior;

attaching said sterilizable plunger rod to said distal end of said syringe body to create a syringe assembly;

sterilizing said syringe assembly; and removably attaching a sterile sheath member to said distal end of said syringe body such that said sterile sheath member covers said outwardly protruding portion of said cannula and establishes a second seal with said distal end of said syringe body which cooperates with said first seal to maintain the sterility of said cannula.

9. The syringe of claim 1 wherein said distal end of said syringe body has a cannula-receiving passage for receiving a portion of said double-ended cannula member therein and wherein said double-ended cannula is removably attached to said distal end of said syringe body, said syringe further comprising a sterilizable stopper member removably attachable to said distal end of said syringe body for creating a secondary seal therebetween when said double-ended cannula member is detached therefrom such that when said sterilizable syringe body and plunger rod have been sterilized and said plunger rod has been attached to said distal end to establish said first seal therebetween, said first and secondary seals maintain the sterility of said cannula receiving passage.

* * * * *